US009456856B2

(12) United States Patent
Ballard

(10) Patent No.: US 9,456,856 B2
(45) Date of Patent: Oct. 4, 2016

(54) INTRABODY OSTEOTOMY IMPLANT AND METHODS OF USE

(71) Applicant: Warsaw Orthopedic, Inc., Warsaw, IN (US)

(72) Inventor: Rodney Ballard, Lakeland, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 252 days.

(21) Appl. No.: 14/037,737

(22) Filed: Sep. 26, 2013

(65) Prior Publication Data

US 2015/0088256 A1  Mar. 26, 2015

(51) Int. Cl.
*A61B 17/58* (2006.01)
*A61B 17/70* (2006.01)

(52) U.S. Cl.
CPC ......... *A61B 17/7083* (2013.01); *A61B 17/708* (2013.01); *A61B 17/7085* (2013.01)

(58) Field of Classification Search
CPC  A61B 17/809; A61B 17/8095; A61B 17/56; A61B 17/70; A61B 17/885; A61B 17/8852; A61B 17/8855; A61B 17/8858
See application file for complete search history.

(56) References Cited

U.S. PATENT DOCUMENTS

| | | | |
|---|---|---|---|
| 6,099,531 A * | 8/2000 | Bonutti | 606/87 |
| 6,190,414 B1 * | 2/2001 | Young et al. | 623/17.15 |
| 6,241,771 B1 | 6/2001 | Gresser et al. | |
| 6,287,308 B1 * | 9/2001 | Betz et al. | 606/263 |
| 6,302,914 B1 | 10/2001 | Michelson | |
| 7,163,558 B2 | 1/2007 | Senegas et al. | |
| 7,238,203 B2 | 7/2007 | Bagga et al. | |
| 8,287,597 B1 * | 10/2012 | Pimenta et al. | 623/17.16 |
| 8,361,149 B2 | 1/2013 | Castro | |
| 8,439,977 B2 | 5/2013 | Kostuik et al. | |
| 2004/0102774 A1 * | 5/2004 | Trieu | 606/61 |
| 2005/0010292 A1 * | 1/2005 | Carrasco | 623/17.11 |
| 2005/0038517 A1 * | 2/2005 | Carrison et al. | 623/17.16 |
| 2005/0228391 A1 * | 10/2005 | Levy et al. | 606/86 |
| 2008/0255615 A1 * | 10/2008 | Vittur et al. | 606/246 |
| 2009/0062917 A1 | 3/2009 | Foley et al. | |
| 2009/0105822 A1 * | 4/2009 | Ogilvie | 623/17.11 |
| 2010/0152782 A1 * | 6/2010 | Stone et al. | 606/280 |
| 2011/0015745 A1 | 1/2011 | Bucci | |
| 2012/0071977 A1 * | 3/2012 | Oglaza et al. | 623/17.11 |
| 2013/0123786 A1 * | 5/2013 | McCormack | A61B 17/1671 606/82 |

FOREIGN PATENT DOCUMENTS

DE  2910627 A1  9/1980

* cited by examiner

*Primary Examiner* — Lynnsy Summitt

(57) ABSTRACT

An intrabody implant disclosed and methods of use are disclosed. The implant has an inclined surface, forming a wedge shape having an acute angle adapted to be placed between at least 2 separated portions of a single bony structure (such as a vertebral body). In some embodiments, the implant may be used to support portions of a vertebral body that have been separated surgically as part of a pedicle subtraction osteotomy and to orient the portions at a more predictable lordotic angle.

19 Claims, 4 Drawing Sheets

INTRABODY OSTEOTOMY IMPLANT AND METHODS OF USE

TECHNICAL FIELD

The present disclosure generally relates to medical devices, systems and methods for the treatment of musculoskeletal disorders, and more particularly, to a wedged intrabody implant and method for fusing portions of a single vertebral body to achieve a desired spinal curvature and/or angulation.

BACKGROUND

Spinal disorders such as degenerative disc disease, disc herniation, osteoporosis, spondylolisthesis, stenosis, scoliosis and other curvature abnormalities, kyphosis, tumor, and fracture may result from factors including trauma, disease and degenerative conditions caused by injury and aging. Spinal disorders typically result in symptoms including pain, nerve damage, and partial or complete loss of mobility. For example, after a disc collapse, severe pain and discomfort can occur due to the pressure exerted on nerves and the spinal column.

Non-surgical treatments, such as medication, rehabilitation and exercise can be effective, however, may fail to relieve the symptoms associated with these disorders. Surgical treatment of these spinal disorders includes fusion, fixation, discectomy, laminectomy, osteotomy and implantable prosthetics. These treatments may employ spinal implants and, in some cases, the placement of interbody implants via a variety of invasive, partially invasive and/or minimally invasive surgical pathways. Furthermore, in spinal disorders wherein a patient has an abnormal spinal curvature, surgeons may perform a complete and/or partial osteotomy to remove bony structures from the spine in order to reorient the bones of the spine to provide the patient with a desired spinal curvature. In many cases, however, there is difficulty in providing an accurate kyphotic and/or lordotic angle when performing osteotomy. Various factors contribute to this difficulty, including, but not limited to: the challenge of cutting a wedge-shaped aperture in the spinal anatomy having a precise slope; and the breakdown or subsidence of the remaining bony portions after an osteotomy is performed. This disclosure describes an improvement in these technologies.

SUMMARY

Accordingly, an intrabody implant and method are disclosed. In one embodiment, an intrabody implant is provided for placement between separated portions of a previously-unitary bony structure, such as a vertebral body. In one embodiment, the intrabody implant comprises first and second surfaces for engaging the first and second portions of the separated bony structure. The surfaces of the implant may be provided with titanium or other coatings or a plurality of surface features extending outward from the surfaces to engage the bony structure. The second implant surface may be disposed opposite the first implant surface at an acute angle relative to the first surface. The implant further comprises a wall disposed between the first and second implant surfaces. The wall comprises anterior and posterior portions wherein the respective heights of the posterior and anterior portions are unequal to form the acute angle.

Various embodiments of the intrabody implant may define an aperture extending through the implant to allow for bone growth through the implant. Furthermore, in some embodiments, the posterior height of the implant may be less than the anterior height of the implant such that the acute angle (which may range widely from 0-90 degrees) introduces a lordotic angle between the first and second portions of the bony structure when the intrabody implant is placed therebetween. The intrabody implant portions may also be formed of a polymer material such as PEEK, and be formed with a convex posterior portion and a concave anterior portion to better conform to the anatomy of the separated bony structure. The implant may also be sized to occupy a substantial width of the bony structure. For example, a width of the implant may, in some embodiments, be greater than 40 mm.

Various method embodiments are also provided for surgically adjusting a curvature of the spine. Such methods may include steps of: removing a wedge-shaped portion of a single vertebral body to form 2 at least partially-separated portions of the vertebral body; providing a wedge-shaped intrabody implant comprising first and second surfaces disposed at an acute angle relative to one another; placing the wedge-shaped intrabody implant between the 2 at least partially-separated portions; and closing the 2 at least partially-separated portions about the implant. The method embodiments may result in the orientation of the 2 at least partially-separated portions of the vertebral body at a correction angle relative to one another.

The method embodiments described herein may provide lordotic and/or kyphotic correction to a spinal column at the level of the single vertebral body or across multiple levels, as part of an osteotomy procedure that may include, but is not limited to, a pedicle subtraction osteotomy (PSO). The closing step disclosed herein may comprise securing the 2 at least partially-separated portions of the single vertebral body relative to one another using a rod and pedicle screw construct. Furthermore, the method may also comprise packing the intrabody implant with bone-growth promotion material (in a bone growth aperture defined in the intrabody implant, for example).

BRIEF DESCRIPTION OF THE DRAWINGS

The present disclosure will become more readily apparent from the specific description accompanied by the following drawings, in which.

DETAILED DESCRIPTION

The exemplary embodiments of an intrabody implant and related methods of use disclosed herein are discussed in terms of medical devices for the treatment of musculoskeletal disorders and more particularly, in terms of an intrabody implant for placement after osteotomy and related methods for treating a vertebral column. It is envisioned that the disclosed intrabody implant and methods may provide, for example, a means for more accurately introducing a correction angle to a portion of the spinal column by virtue of the intrabody implant, which may enable a surgeon to more precisely predict the closure and/or correction angle despite variations in wedge angle that may be introduced in the "bone-on-bone" closure of known osteotomy procedures. In one embodiment, the wedge design of the intrabody implant may aid in the maintenance of anterior vertebral body height while allowing for closure (height collapse) on a posterior portion of the same vertebral body in order to introduce a corrective angulation.

The various embodiments described herein may also be especially useful in maintaining the shape and position of the vertebral body during and after an osteotomy. For example, in known osteotomy procedures as a wedge-cut vertebral body (see FIG. 2, for example) collapses, the anterior portion of the vertebral body (V1, V2) may also break during closure of the angle θ. It may be difficult for a surgeon to predict any shifts that may occur once the anterior portion of the vertebral body breaks. Thus, the intrabody implant 100 (see FIG. 3, for example) may help restrict any shift in the bony structures V1, V2 remaining after an osteotomy procedure.

Figure 1:
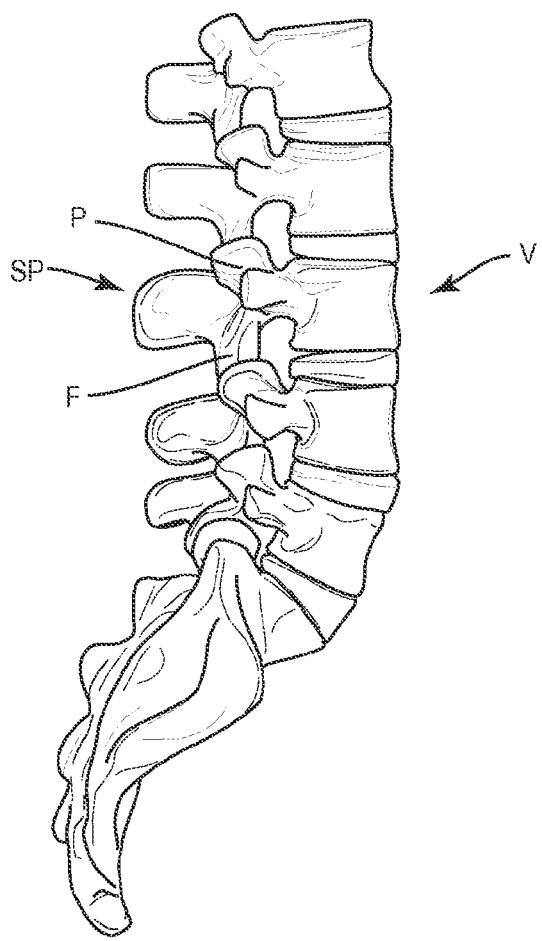
FIG. 1 is a perspective view of a spine with insufficient lordosis in the lumbar region.
Figure 2:
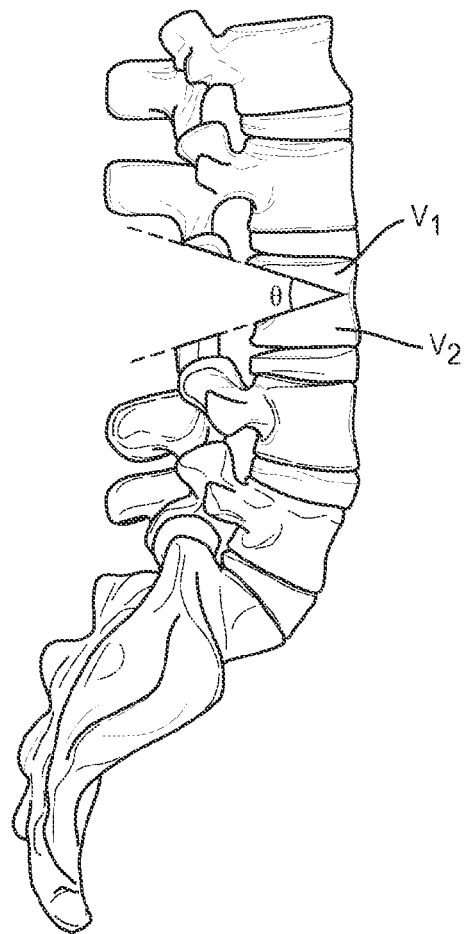
FIG. 2 is a perspective view of a spine after the initial removal of bony material from an osteotomy procedure.
Figure 3:
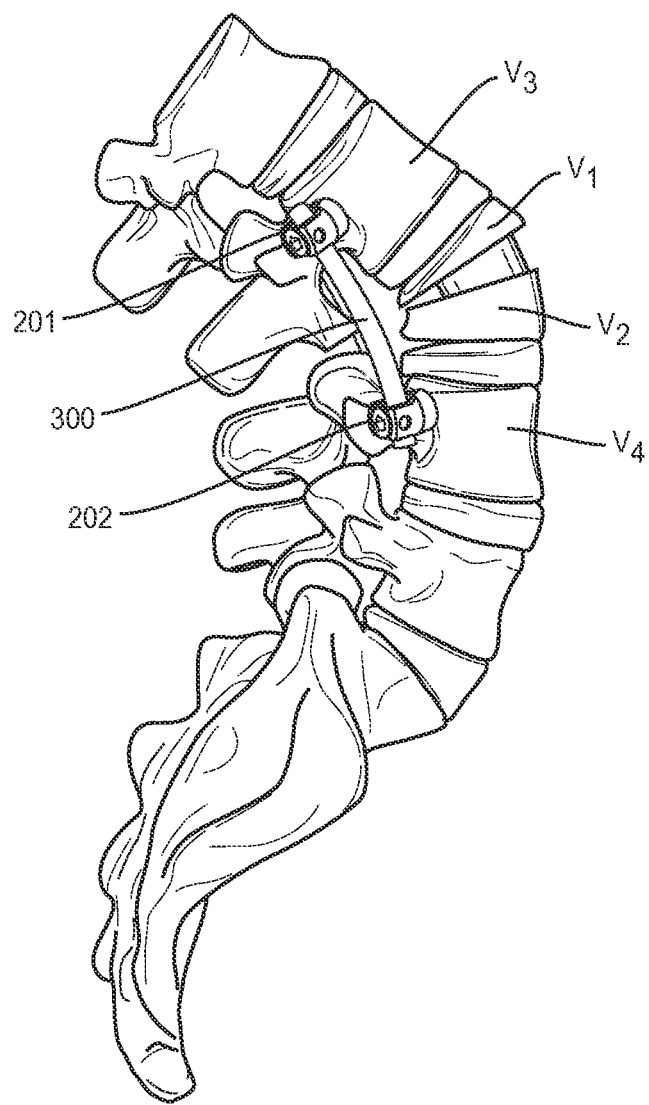
FIG. 3 is a perspective view of a spine with an intrabody implant, according to one embodiment.

Referring to FIGS. 1-3, a method for surgically adjusting a curvature of the spine is provided. In one embodiment, a vertebral body V is selected for an osteotomy procedure which may include removing portions of the pedicle P, spinous processes SP and/or facet joint structures F at the level of the vertebral body V. While level L3 is depicted in FIG. 1, a surgeon may apply the procedure described herein to any number of spinal levels in the lumbar, thoracic, or cervical spine to introduce a corrective curvature to the spine.

As shown in FIG. 2, the method may further comprise removing a wedge-shaped portion of a single vertebral body V (see FIG. 1) to form 2 at least partially-separated portions V1, V2 of the single vertebral body V. A surgeon may select and/or measure a corrective angle θ to serve as the basis for this step. However, and as described further herein, the acute angle α defined by the surfaces 110, 120 of the implant 100 (see FIG. 5) may be used to ensure that the completed spinal surgery results in a desired level of spinal curvature (see FIG. 3) regardless of the angle θ of the removal cut made by the surgeon as part of the removal step. 15. As described herein with respect to FIG. 1, the removing step may comprise a pedicle subtraction osteotomy (PSO) procedure wherein the pedicle P, spinous process SP, and/or portions of the facet joint structure F are completely or partially removed from the vertebral body.

Figure 4:
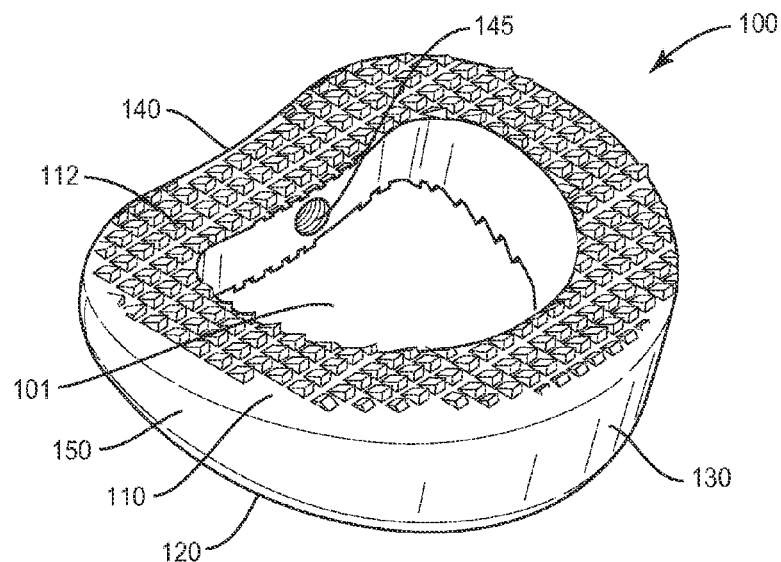
FIG. 4 is a perspective view of an intrabody implant, according to one embodiment.

The method may further comprise providing a wedge-shaped intrabody implant 100 (as described further herein with respect to FIGS. 4-6) comprising a first surface 110 and a second surface 120, wherein the second surface 120 may be disposed at an acute angle α to the first surface 110. In some embodiments as shown in FIG. 4, the intrabody implant 100 may be provided with an aperture 101 extending through the wedge-shaped intrabody implant 100 to allow for bone growth therethrough. In other embodiments, the method may further comprise packing the aperture 101 with a bone-growth promotion material prior to the placing step described herein with respect to FIG. 3.

As shown in FIG. 3, the method further comprises placing the wedge-shaped intrabody implant 100 between the 2 at least partially-separated portions V1, V2 of the single vertebral body V, and closing the 2 at least partially-separated portions V1, V2 of the single vertebral body about the intrabody implant 100. Therefore, the 2 at least partially-separated portions V1, V2 of the single vertebral body are oriented at a correction angle relative to one another. Preferably, the resulting correction angle may be substantially predictable based on the selected implant. For example, in some embodiments, the correction angle may be within a selected number of degrees of the acute angle defined by the intrabody implant. In some embodiments, the range of difference between the correction angle and the acute angle may be relatively wide (i.e. 10-90 degrees). In other embodiments, the range of difference between the correction angle and the acute angle may be relatively narrow (i.e. 0-10 degrees).

According to various method embodiments, the correction angle of the spinal column defined at least in part by the acute angle α of the intrabody implant may provide a lordotic correction to a spinal column at the level of the single vertebral body V. In other embodiments, the implant direction may be reversed such that the correction angle of the spinal column defined at least in part by the acute angle α of the intrabody implant may provide a kyphotic correction to a spinal column at the level of the single vertebral body V. In some embodiments, the various embodiments of the present invention may provide a correction angle across multiple levels (such that the acute angles α of several intrabody implants 100 may provide a lordotic correction to a spinal column across 2 or more levels). In such embodiments, the removing, providing, placing and closing steps disclosed herein may be repeated across two or more levels of the human spine to achieve an overall spinal correction across the two or more levels.

Figure 7:
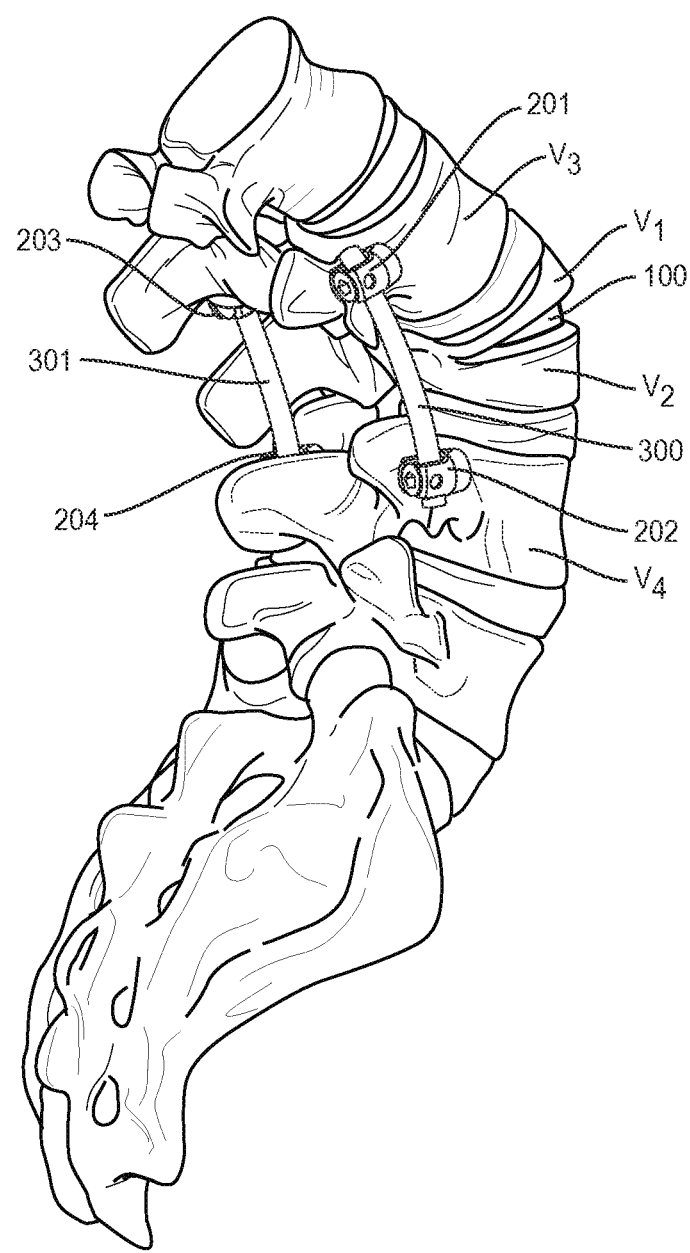
FIG. 7 is a perspective view of a spine with an intrabody implant system, according to one embodiment.

In some method embodiments, the closing step described herein may further comprise securing the 2 at least partially separated portions V1, V2 of the vertebral body V about the implant 100 using an extradiscal stabilization system (which may include, for example, a rod 300 and pedicle screw 201, 202 construct as shown generally in FIGS. 3 and 7. The pedicle screws 201, 202 may be inserted into the pedicles of adjacent vertebral bodies V3, V4 and connected via rod 300 that may be shaped and/or bent by the surgeon to further reinforce the corrective angle sought as part of the surgical procedure. FIG. 7 shows a perspective view of a bi-lateral screw 201, 202, 203, 204 and rod 300, 301 construct that may also be used to reinforce the corrected spinal curvature using the various methods described here. Various screw and rod systems may be used for the reinforcement step, including but not limited to the SOLERA® and LEGACY® extradiscal stabilization systems offered by Medtronic® Spine.

Referring now to FIGS. 3-6, an intrabody implant 100 is disclosed for placement between at least 2 separated portions V1, V2 of a bony structure such as a vertebral body V. The implant 100 may be formed in whole or in part from a variety of biocompatible materials suitable for long-term implantation. For example, the implant 100 may be preferably formed of a polymer such as PEEK.

The components of implant 100 can be fabricated from a variety of biologically acceptable materials suitable for medical applications, including metals, synthetic polymers, ceramics and bone material and/or their composites, depending on the particular application and/or preference of a medical practitioner. For example, the components of implant 100, individually or collectively, can be fabricated from materials such as stainless steel alloys, commercially pure titanium, titanium alloys, Grade 5 titanium, superelastic titanium alloys, cobalt-chrome alloys, stainless steel alloys, superelastic metallic alloys (e.g., Nitinol, super elasto-plastic metals, such as GUM METAL® manufactured by Toyota Material Incorporated of Japan), ceramics and composites thereof such as calcium phosphate (e.g., SKEL-ITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-$BaSO_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate such as hydroxyapatite (HA), corraline HA, biphasic calcium phosphate, tricalcium phosphate, or fluorapatite, tri-calcium phosphate (TCP), HA-TCP, calcium sulfate, or other resorbable polymers such as polyaetide, polyglycolide, polytyrosine carbonate, polycaroplaetohe and their combinations, biocompatible ceramics, mineralized collagen, bioactive glasses, porous metals, bone particles, bone fibers, morselized bone chips, bone morphogenetic proteins (BMP), such as BMP-2, BMP-4, BMP-7, rhBMP-2, or rhBMP-7, demineralized bone matrix (DBM), transforming growth factors (TGF, e.g., TGF-β), osteoblast cells, growth and differentiation factor (GDF), insulin-like growth factor 1, platelet-derived growth factor, fibroblast growth factor, or any combination thereof.

Figures 5, 6:
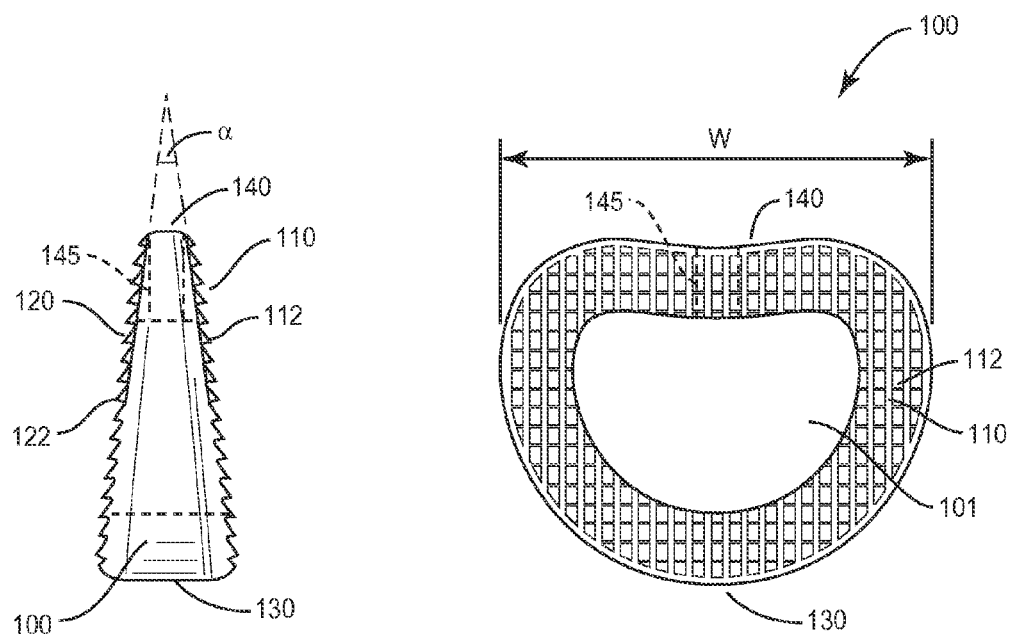
FIG. 5 is a side view of an intrabody implant, according to one embodiment.
FIG. 6 is a top view of an intrabody implant, according to one embodiment.

According to the various embodiments provided herein, the implant 100 may comprise a first surface 110 configured for engaging a first V1 of the at least two separated portions of the bony structure. The implant 100 further comprises a second surface 120, disposed opposite the first surface 110, and configured for engaging a second V2 of the at least two separated portions of the bony structure. As shown in FIG. 5, the first and second surfaces 110, 120 may be disposed at an acute angle a relative to one another. The angle α may range widely from zero to 90 degrees. However, in some preferable embodiments the angle a may range from 10 to 30 degrees. In other more preferable embodiments, the angle a may range from 15 to 25 degrees.

As shown in FIGS. 4 and 5, the implant 100 may further comprise a wall 150 disposed between the first and second surfaces 110, 120. The wall 150 comprises an anterior portion 130 and a posterior portion 140. As shown in FIG. 5, the posterior portion 140 has a posterior height and the anterior portion 130 has an anterior height, wherein the posterior and anterior heights are unequal to form the preferably acute angle a between the first surface 110 and the second surface 120 of the implant 100. In some embodiments, as shown in FIG. 5, the posterior height may be less than the anterior height such that the angle a of the implant 100 introduces a lordotic angle between the first and second portions V1, V2 of the bony structure V (see FIG. 3, for example). Furthermore, as shown in FIG. 5, the posterior portion 140 and/or anterior portion 130 of the implant may be provided with a convex profile between the first and second surfaces 110, 120 to aid in the ease of insertion of the implant 100. The profile may also, in alternate embodiments, be chamfered and/or provided with edge radii to allow for easier insertion of the implant 100 from either the posterior or anterior directions.

FIG. 6 shows a top view of an implant 100 according to one embodiment wherein the first and second surfaces 110, 120 define an aperture 101 extending through the implant 100 to allow for bone growth through the implant 100 from the first portion V1 of the bony structure V to the second portion V2 (see FIG. 3, for example). The aperture 101 may also be packed with bone growth promoting material, including but not limited to bone allograft, bone xenograft, bone autograft, bone morphogenetic protein (BMP) and/or combinations thereof. Furthermore, as shown in FIG. 6, the implant 100 may be formed in a shape that conforms to the anatomy of the human spine. For example, the posterior portion 140 of the wall 150 may comprise an outer concave surface configured to conform to a posterior anatomy of the bony structure V. Furthermore, the anterior portion 130 of the wall 150 may comprise an outer convex surface configured to conform to an anterior anatomy of the bony structure V.

Referring again to FIG. 6, the implant 100 may include a width W extending substantially parallel to the anterior portion 130 and the posterior portion 140. The width W of the implant 100 may be chosen to substantially fill the width of the vertebral body V or other bony structure where the intrabody is intended to be placed after osteotomy. For example, in some embodiments, the width W may be at least 40 mm. In other embodiments, the width W may be at least 50 mm (when used, for example, in the lower lumbar region). In other embodiments, the width W may be tailored for use in smaller vertebral bodies (for example, in smaller patients or in the upper thoracic or cervical spine). In some such embodiments, the width W may be in the range of 15-40 mm (or 25-30 mm in some preferable cervical and thoracic embodiments). The depth of the implant 100 may also vary accordingly (wherein the depth is measured perpendicular to the width W from the anterior portion 130 to the posterior portion 140). In some embodiments, the depth may range from 10 mm to 50 mm (and preferably from 15-20 mm in certain embodiments).

As shown in FIGS. 4 and 6, the first surface 110 and second surface 120 of the implant 100 may further comprise a plurality of surface features 112 extending outward from the surfaces 110, 120 to engage a complementary surface of the bony structure V. For example, the surface features 112 may include, but are not limited to: ridges, teeth, pyramidal structures, roughened irregular projections and/or combinations thereof. The surface features 112 may be optimized in shape and/or directional orientation to resist the expulsion of the implant 100 from between the portions V1, V2 of the bony structure when the patient applies weight forces to the spine during the course of standing or movement. For example, the surface features 112, may comprise rows of teeth (see FIG. 5) having a substantially right-triangular profile wherein the teeth are sloped upwards towards the anterior portion 130 of the wall 150 of the implant 100. In other embodiments, the implant 100 may further comprise a coating applied to one or more of the surfaces 110, 120 and/or the wall 150 to encourage bone growth onto the implant 100. Such coatings may include, but are not limited to: gold, titanium, hydroxyapatite (HA) and/or combinations thereof. The coatings may be applied with a roughened texture so as to provide a plurality of irregular projections that may serve as surface features 112 to also resist expulsion of the implant 100 after implantation. In other embodiments, the implant 100 may have substantially smooth surfaces 110, 120 and wall 150 having no projections or surface features.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A method for surgically adjusting a curvature of a spine comprising vertebrae, the method comprising:
    removing a wedge-shaped portion of a single vertebral body of the vertebrae to form 2 at least partially-separated portions of the single vertebral body;
    providing a wedge-shaped intrabody implant comprising a first surface and a second surface, the second surface disposed at an acute angle to the first surface;
    placing the wedge-shaped intrabody implant between the 2 at least partially-separated portions of the single vertebral body;
    inserting threaded pedicle screws into the vertebrae such that each of the screws is spaced apart from the implant; and
    closing the 2 at least partially-separated portions of the single vertebral body about the intrabody implant, wherein closing comprises connecting the screws with a rod, such that the 2 at least partially-separated portions of the single vertebral body are oriented at a correction angle relative to one another.

2. The method as recited in claim 1, wherein the correction angle provides a lordotic correction to a spinal column at the level of the single vertebral body.

3. The method as recited in claim 2, wherein the acute angle is between 10 degrees and 30 degrees.

4. The method as recited in claim 2, wherein the acute angle is between 15 degrees and 25 degrees.

5. The method as recited in claim 1, wherein the correction angle provides a kyphotic correction to a spinal column at the level of the single vertebral body.

6. The method as recited in claim 1, wherein the removing step comprises a pedicle subtraction osteotomy (PSO) procedure.

7. The method as recited in claim 1, further comprising repeating the removing, providing, placing and closing steps across two or more levels of the spine to achieve an overall spinal correction across the two or more levels.

8. The method as recited in claim 7, further comprising, packing an aperture in the implant with a bone-growth promotion material prior to the placing step.

9. The method as recited in claim 1, wherein the screws are spaced apart from the single vertebral body.

10. The method as recited in claim 1, wherein inserting threaded pedicle screws inserting another of the screws into the vertebrae consists of inserting one of the screws into a second vertebral body that is superior to the single vertebral body and into a third vertebral body that is inferior to the single vertebral body.

11. The method as recited in claim 1, wherein the first and second surfaces each include rows of teeth.

12. The method as recited in claim 1, wherein the first and second surfaces each include rows of teeth, the teeth each having a substantially right-triangular profile such that the teeth are sloped upwards towards an anterior portion of the implant.

13. The method as recited in claim 1, wherein placing the wedge-shaped intrabody implant comprises positioning an outer concave surface of a posterior portion of the implant such that the outer concave surface conforms to a posterior anatomy of the single vertebral body.

14. The method as recited in claim 1, wherein placing the wedge-shaped intrabody implant comprises positioning an outer convex surface of an anterior portion of the implant such that the outer convex surface conforms to an anterior anatomy of the single vertebral body.

15. A method for surgically adjusting a curvature of a spine, the method comprising:
    removing a wedge-shaped portion of a single vertebral body to form 2 at least partially-separated portions of the single vertebral body;
    providing a wedge-shaped intrabody implant comprising a first surface and a second surface, the second surface disposed at an acute angle to the first surface;
    placing the implant between the 2 at least partially-separated portions of the single vertebral body such that an outer concave surface of a posterior portion of the implant conforms to a posterior anatomy of the single vertebral body and an outer convex surface of an anterior portion of the implant conforms to an anterior anatomy of the single vertebral body; and
    closing the 2 at least partially-separated portions of the single vertebral body about the implant such that the 2 at least partially-separated portions of the single vertebral body are oriented at a correction angle relative to one another.

16. The method as recited in claim 15, wherein the outer convex surface is free of any openings.

17. The method as recited in claim 15, wherein the spine comprising vertebrae, the single vertebral body being one of the vertebrae;
    the method further comprises inserting threaded pedicle screws into the vertebrae such that each of the screws is spaced apart from the implant; and
    closing the 2 at least partially-separated portions comprises connecting the screws with a rod.

18. A method for surgically adjusting a curvature of a spine, the method comprising:
    removing a wedge-shaped portion of a single vertebral body to form 2 at least partially-separated portions of the single vertebral body;
    providing a wedge-shaped intrabody implant comprising a first surface and a second surface, the second surface disposed at an acute angle to the first surface;
    placing the wedge-shaped intrabody implant between the 2 at least partially-separated portions of the single vertebral body;
    inserting first threaded pedicle screws into vertebrae adjacent to the single vertebral body such that the first threaded pedicle screws are positioned on a left lateral side of spinous processes of the vertebrae adjacent to the single vertebral body;
    inserting second threaded pedicle screws into the vertebrae adjacent to the single vertebral body such that the second threaded pedicle screws are positioned on a right lateral side of the spinous processes of the vertebrae adjacent to the single vertebral body; and
    closing the 2 at least partially-separated portions of the single vertebral body about the intrabody implant, wherein closing comprises connecting the first threaded pedicle screws with a first rod and connecting the second threaded pedicle screws with a second rod, such that the 2 at least partially-separated portions of the single vertebral body are oriented at a correction angle relative to one another.

19. The method as recited in claim 18, wherein placing the wedge-shaped intrabody implant comprises positioning an outer concave surface of a posterior portion of the implant such that the outer concave surface conforms to a posterior anatomy of the single vertebral body and positioning an outer convex surface of an anterior portion of the implant such that the outer convex surface conforms to an anterior anatomy of the single vertebral body.

* * * * *

UNITED STATES PATENT AND TRADEMARK OFFICE
CERTIFICATE OF CORRECTION

| | | |
|---|---|---|
| PATENT NO. | : 9,456,856 B2 | Page 1 of 1 |
| APPLICATION NO. | : 14/037737 | |
| DATED | : October 4, 2016 | |
| INVENTOR(S) | : Ballard | |

It is certified that error appears in the above-identified patent and that said Letters Patent is hereby corrected as shown below:

In the Specification

In Column 5, Line 26, delete "corraline HA," and insert -- coralline HA, --, therefor.

In the Claims

In Column 7, Line 56, in Claim 10, delete "inserting another of the screws" and insert the same after "body and" as a continuation paragraph.

Signed and Sealed this
Seventeenth Day of January, 2017

Michelle K. Lee
*Director of the United States Patent and Trademark Office*